US009192455B1

(12) United States Patent
Moses et al.

(10) Patent No.: US 9,192,455 B1
(45) Date of Patent: Nov. 24, 2015

(54) ORAL APPLIANCES AND METHODS OF MAKING ORAL APPLIANCES

(71) Applicants: Allen J. Moses, Chicago, IL (US);
Gloria L. Pacini, Orland Park, IL (US)

(72) Inventors: Allen J. Moses, Chicago, IL (US);
Gloria L. Pacini, Orland Park, IL (US)

( * ) Notice: Subject to any disclaimer, the term of this patent is extended or adjusted under 35 U.S.C. 154(b) by 29 days.

(21) Appl. No.: 13/774,550

(22) Filed: Feb. 22, 2013

Related U.S. Application Data

(62) Division of application No. 13/014,848, filed on Jan. 27, 2011, now Pat. No. 8,646,454.

(51) Int. Cl.
*A61C 9/00* (2006.01)

(52) U.S. Cl.
CPC ........................................ *A61C 9/00* (2013.01)

(58) Field of Classification Search
CPC ........ A61C 9/00; A61C 9/0006; A61C 9/004; A61C 9/008; A61C 9/0093
USPC ............ 433/37, 71, 6, 24, 213–214; 128/848, 128/859–862
See application file for complete search history.

(56) References Cited

U.S. PATENT DOCUMENTS

| | | | | |
|---|---|---|---|---|
| 4,543,062 A | * | 9/1985 | Lee | 433/71 |
| 5,346,395 A | | 9/1994 | Adell | |
| 5,562,106 A | | 10/1996 | Heeke et al. | |
| 5,692,521 A | * | 12/1997 | Leasure-Nelson | A61F 5/566 128/848 |

OTHER PUBLICATIONS

Miscellaneous Declaration by Inventor, Jan. 16, 2012, and related brochure for the Moses™ product.
Allen J. Moses, DDS; Evolution of Theory on Oral Appliances and Exercises for Sleep Apnea and Snoring; Article; Sleep Diagnosis and Therapy, vol. 5, No. 7 Nov.-Dec. 2010; pp. 22-25.
Allen J. Moses, DDS; J. A. Bedoya and J. A. Learreta; Case Study of the Anatomic Changes Effected by a Mandibular Advancement Device in a Sleep Apnea Patient; Article; Sleep Diagnosis and Therapy, vol. 5, No. 1 Jan.-Feb. 2010; pp. 30-34.
Allen J. Moses, DDS, DABCP, DABDSM; What's New in Oral Appliances for Snoring and Sleep Apnea; Editorial, Sleep Diagnosis and Therapy, vol. 2, No. 6 Dec. 2007; pp. 19-24.

* cited by examiner

*Primary Examiner* — Yogesh Patel
(74) *Attorney, Agent, or Firm* — McAndrews, Held & Malloy, Ltd.

(57) ABSTRACT

Oral appliances, methods of making oral appliances, and bite registration devices for use in making oral appliances are provided. An oral appliance includes a lower segment, and upper segments. The upper segments are operably connected to the lower segment using threaded elements. Rotational manipulation of the threaded elements causes the upper segments to be displaced horizontally relative to the lower segment about the lengths of the threaded elements, and the lengths of the threaded elements are substantially parallel to each other. A bite registration device for use in making an oral appliance includes a top surface including a protrusion and a bottom surface including a receptacle configured to receive the protrusion. The device is configured to be maintained in stacked relation to a like configured second bite registration device by mating the protrusion of the bite registration device with a receptacle of the second bite registration device.

12 Claims, 10 Drawing Sheets

ORAL APPLIANCES AND METHODS OF MAKING ORAL APPLIANCES

CROSS-REFERENCE TO RELATED APPLICATIONS/INCORPORATION BY REFERENCE

This application makes reference and claims priority to U.S. patent application Ser. No. 13/014,848, filed on Jan. 27, 2011, titled "Oral Appliances And Methods Of Making Oral Appliances." This application is a divisional of U.S. patent application Ser. No. 13/014,848. U.S. patent application Ser. No. 13/014,848 is hereby incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention is in the technical field of dentistry. More particularly, an oral appliance and method of making an oral appliance are provided, including a bite registration device for use by dentists to determine and record the correct patient bite position for a laboratory to fabricate an oral appliance.

The airway of humans has no bony support. This unique condition has the distinct advantage of facilitating speech, a very valuable adaptation, but has disadvantages as well—choking, snoring and apnea. Snoring and obstructive Sleep Apnea Syndrome ("OSAS") are the manifestations of collapse of the flexible, compliant human airway.

Snoring is defined as obstructive sleep breathing, characterized by a harsh, loud sound. Snoring is a partial collapse of the tongue on the airway. Three conditions are necessary for snoring to occur: (1) sleep, (2) airflow limitation, and (3) vibrating structure in the airway. Snoring is a condition affecting approximately 40% of the population. Snoring can disrupt the sleep, not only of the snorer, but the sleep partner as well, having profound effects on their daytime quality of life.

OSAS has been reported to occur in up to 7 or 8% of the population. The tongue during sleep loses it natural tonus and can collapse into the airway, blocking airflow. Apnea literally means lack of breath. OSAS is a condition that occurs during sleep when a person is trying to breathe and get air, but the airway is blocked by the tongue. Airway blockage for a period of at least 10 seconds with effort being made to breathe is the definition of an apneic event. The apneic blockage is ended by a gasp, causing an arousal that disrupts normal sleep architecture.

The four commonly utilized therapies to treat snoring and sleep apnea are CPAP (continuous positive air pressure) therapy, surgery, lifestyle changes and oral airway dilators. CPAP works well, but it is uncomfortable, requires wearing a mask attached to a positive pressure pump, and creates a bloated feeling. Surgery is painful and invasive, and has a success rate of less than 50%. Lifestyle changes such as weight loss, exercise, no alcohol consumption, dietary counseling and food restrictions have very low compliance. Oral airway dilators have high patient compliance, and are comfortable and effective, particularly in cases of mild to moderate OSAS. The drawbacks of known oral airway devices are that some restrict tongue protrusion by their design of anterior mandibular advancement mechanisms, some cause tooth movement by incorporating retentive clasps on teeth, others cause gagging by tongue depression, and some have frequent breakage. The color of many such devices, which are constructed with clear methyl-methacrylate material, deteriorate in color with time, becoming an unpleasant shade of yellow.

Further, when fabricating an oral dental device, such as an oral airway dilator, for example, the prescribing dentist must determine the relationship in space in all dimensions of the mandibular (lower) arch in relation to the maxillary (upper) arch. Bite registration devices are provided between the patient's upper and lower arches and record an imprint of the patient's maxillary and mandibular teeth and ridges in the prescribed position. The bite registration is later used by a laboratory along with stone casts that are made from impressions of the patient's upper and lower arches. The stone casts are mounted on an articulator with the bite registration between the maxillary and mandibular arches in the exact position that the dentist prescribes. This process facilitates the proper fit of the oral dental device for the patient.

Historically, wax was the substance used to record the patient's bite. However, a bite recorded in wax is not stable as it may warp, bend and/or become brittle, depending on how it is handled and stored. If any of these above occurrences happens to the wax bite, the bite will not be a proper replica of the relationship between the maxillary and mandibular arches.

Certain conventional bite registration devices require the lips to be separated in order to record a full arch bite. Breathing through the nose with the lips closed is the healthiest physiological condition for sleep. If an individual's jaws are so far apart that he or she cannot comfortably close the lips, he or she will breathe through the mouth. The lips should be closed when the future oral dental device is in the mouth.

Certain conventional bite registration devices may not allow the distance between a patient's maxillary and mandibular arches to be easily varied. However, it may be desirable for a prescribing dentist to select a custom distance between a patient's maxillary and mandibular arches.

In light of the foregoing, there is a need for improved oral airway dilators and methods of making oral appliances. Such improved methods of making may include improved bite registration devices.

SUMMARY OF THE INVENTION

Certain embodiments of the present technology provide an oral appliance comprising: a first component including a lower segment, a first upper segment and a second upper segment, the lower segment configured to substantially conform to contours of a plurality of a user's lower teeth, the first upper segment configured to conform to contours of a first plurality of the user's upper teeth, the second upper segment configured to conform to contours of a second plurality of the user's upper teeth, the first upper segment operably connected to the lower segment using a first threaded element such that rotational manipulation of the first threaded element causes the first upper segment to be displaced horizontally relative to the lower segment about a length of the first threaded element, the second upper segment operably connected to the lower segment using a second threaded element such that rotational manipulation of the second threaded element causes the second upper segment to be displaced horizontally relative to the lower segment about a length of the second threaded element, the length of the first threaded element and the length of the second threaded element being substantially parallel to each other.

In certain embodiments, the lower segment includes an interior lingual flange with a thickness of at least about 3 millimeters.

In certain embodiments, the lower segment includes ridges extending anteriorly and upward from distolingual corners of the lower segment.

In certain embodiments, the lower segment extends behind the user's teeth, wherein the lower segment does not extend over the top or in front of the user's anterior teeth, and wherein the lower segment extends over the top and in front of the user's posterior teeth.

In certain embodiments, an oral appliance also includes a second component configured to substantially conform to contours of a plurality of a user's upper teeth, the second component including a plurality of raised surfaces located at lingual incisal edges of one or more incisors.

In certain embodiments, the second component is configured to matingly engage the first and second upper segments such that, when maintained in a user's mouth, the user's upper teeth and lower teeth are maintained apart and in a fixed mandibular position.

In certain embodiments, the first component comprises a translucent, non-clear material.

Certain embodiments of the present technology provide a method of making an oral appliance comprising: forming a first component including a lower segment, a first upper segment and a second upper segment, the lower segment configured to substantially conform to contours of a plurality of a user's lower teeth, the first upper segment configured to conform to contours of a first plurality of the user's upper teeth, the second upper segment configured to conform to contours of a second plurality of the user's upper teeth; operably connecting the first upper segment to the lower segment using a first threaded element such that rotational manipulation of the first threaded element can cause the first upper segment to be displaced horizontally relative to the lower segment about a length of the first threaded element; and operably connecting the second upper segment to the lower segment using a second threaded element such that rotational manipulation of the second threaded element can cause the second upper segment to be displaced horizontally relative to the lower segment about a length of the second threaded element, wherein the length of the first threaded element and the length of the second threaded element are substantially parallel to each other.

In certain embodiments, a method further includes forming ridges on the lower segment, the ridges extending anteriorly and upward from distolingual corners of the lower segment.

In certain embodiments, a method further includes forming a second component configured to substantially conform to contours of a plurality of a user's upper teeth; and forming on the second component a plurality of raised surfaces located at lingual incisal edges of one or more incisors.

In certain embodiments, the first component is formed using a translucent, non-clear material.

In certain embodiments, a method further includes using a bite registration device to capture the user's bite position.

In certain embodiments, a method further includes stacking two or more bite registration devices such that they are maintained in stacked relation, thereby providing a first bite registration device; positioning the first bite registration device into a user's mouth; applying a bite-recording material to the first bite registration device around the user's teeth and gums; and allowing the bite-recording material to mechanically adhere to the first bite registration device, thereby capturing the user's bite position.

In certain embodiments, a method further includes positioning a second bite registration device into the user's mouth such that the first bite registration device and the second bite registration device abut at a planar surface; and slidably adjusting the relative position of the first bite registration device and the second bite registration device while maintaining abutment therebetween by manipulating the position of the user's mandible.

In certain embodiments, a method further includes applying the bite-recording material to the second bite registration device around the user's teeth and gums; and allowing the bite-recording material to mechanically adhere to the second bite registration device, thereby capturing the user's bite position.

In certain embodiments, each stacked bite registration device includes: a first surface including a protrusion; and a second surface opposite the first surface, the second surface including a receptacle configured to receive the protrusion, wherein the devices are maintained in stacked relation by mating a protrusion of a first device with a receptacle of a second device.

Certain embodiments of the present technology provide a bite registration device for use in making an oral appliance comprising: a first surface including a protrusion; and a second surface opposite the first surface, the second surface including a receptacle configured to receive the protrusion, wherein the bite registration device is configured to be maintained in stacked relation to a like configured second bite registration device by mating the protrusion of the bite registration device with a receptacle of the second bite registration device.

In certain embodiments, the first surface includes a groove configured to retain bite-recording material on the bite registration device.

In certain embodiments, a bite registration device further includes an arched front edge connecting the first surface and the second surface, the arched front edge configured to be adjacent to a user's lips when the bite registration device is maintained in the user's mouth such that the bite registration device does not protrude beyond the user's closed lips when the bite registration device is maintained in the user's mouth.

In certain embodiments, a bite registration device further includes an arched rear edge opposite the arched front edge, the arched rear edge configured to be adjacent to the user's tongue when the bite registration device is maintained in the user's mouth.

In certain embodiments, a bite registration device further includes a plurality of non-linear edges connecting the arched front edge and the arched rear edge, the non-linear edges configured to retain bite-recording material on the bite registration device.

In certain embodiments, the first surface is configured to face toward a user's teeth during a bite registration procedure.

In certain embodiments, the second surface is configured to face away from a user's teeth during a bite registration procedure.

In certain embodiments, the second surface is planar.

BRIEF DESCRIPTION OF THE DRAWING(S)

Figure 1:
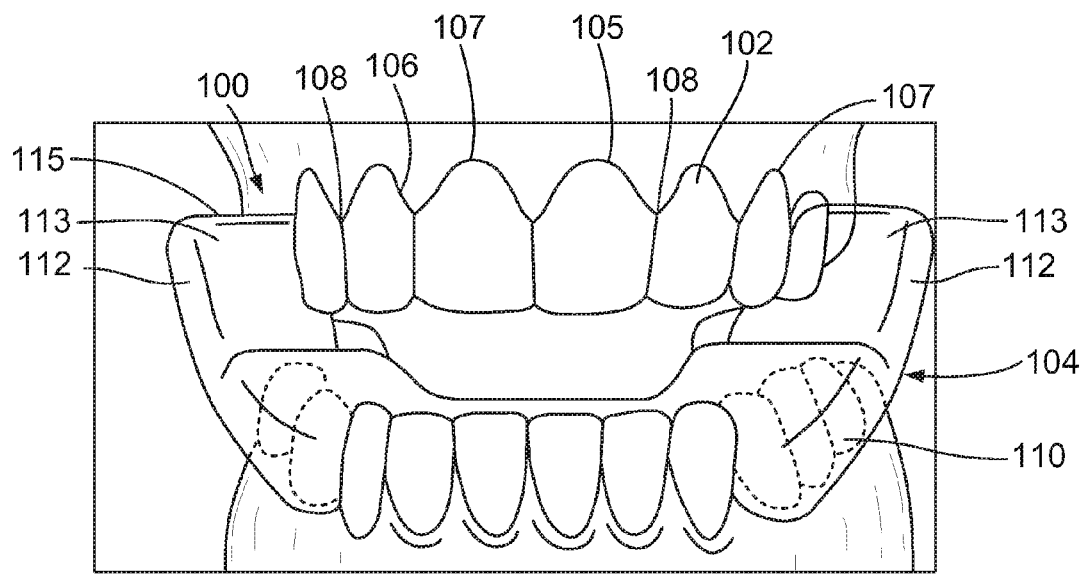
FIG. 1 is a front view of an oral appliance used in accordance with an embodiment of the present technology.
Figure 2:
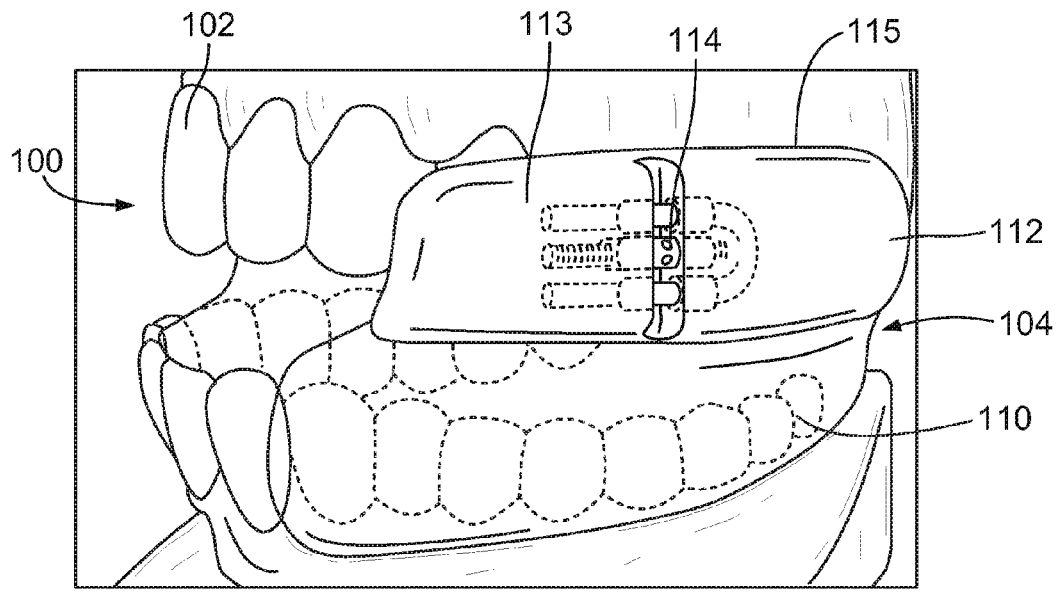
FIG. 2 is a side view of the oral appliance of FIG. 1.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentalities shown in the attached drawings.

DETAILED DESCRIPTION OF PREFERRED EMBODIMENT(S)

Embodiments of the present technology provide an improved oral appliance and methods of making oral appliances. Improved methods of making can include use of an improved bite registration device, as provided herein, for example.

In certain embodiments, an oral appliance as described herein can be used to treat, for example, sleep apnea, snoring, nocturnal tooth grinding and clenching, movement of teeth during sleep, rhythmic bruxism, certain temporomandibular disorders and/or some muscle tension headaches. Certain embodiments of oral appliances described herein, when made to a prescribed bite, can dilate a user's airway when placed in the mouth, thereby preventing collapse of the tongue on the soft palate and the airway when the user is asleep. Certain embodiments of oral appliances described herein can position a user's mandible in a protrusive position of low muscle activity and increase volume of space for the tongue. Certain embodiments of oral appliances described herein can facilitate training of protrusive and non-retrusive tongue reflexes. Certain embodiments of oral appliances described herein can provide improved resistance to discoloration or staining of the oral appliance. Certain embodiments of oral appliances described herein can allow a user to drink and/or talk while wearing the appliance.

An embodiment of the present technology will now be described in connection with the figures, where like elements are identified with like numerals. FIG. 1 is a front view of an oral appliance 100 used in accordance with an embodiment of the present technology. FIGS. 2-6 provide various other views of oral appliance 100 or components thereof.

Oral appliance 100 includes upper component 102 and lower component 104. In certain embodiments, upper component 102 and/or lower component 104 can comprise a non-clear material, such as a translucent blue or opaque tooth color, for example. It has been found that such non-clear oral appliances can provide improved resistance to staining and/or color change.

Upper component 102 is configured to be received on a user's upper (maxillary) teeth and is formed to substantially conform to the contours of the user's upper teeth. Upper component 102 includes an upper edge 105 comprising wavy scallops 106 configured to replicate a user's gum line. In certain embodiments, upper edge 105 is configured such that it will not contact the user's gums. Wavy scallops 106 include curved apexes 107 that occur toward the middle of each tooth, and curved valleys 108 that occur between teeth. It has been found that curved apexes 107 and curved valleys 108 can avoid tearing associated with pointed apexes and valleys.

Upper component 102 spans a user's entire upper dental arch, including the rearmost molars. In certain embodiments, an upper component may not span a user's full upper dental arch.

Figure 3:
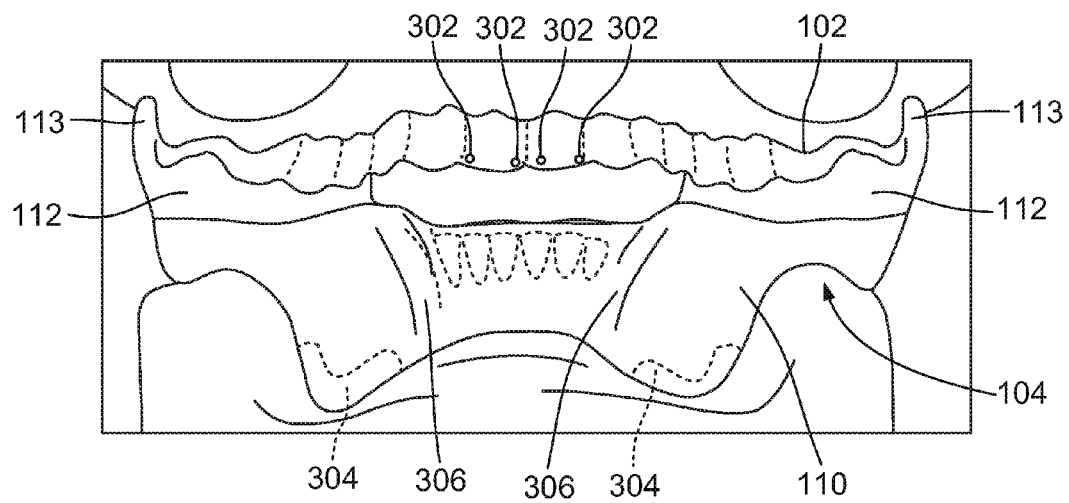
FIG. 3 is a rear view of the oral appliance of FIG. 1.
Figure 6:
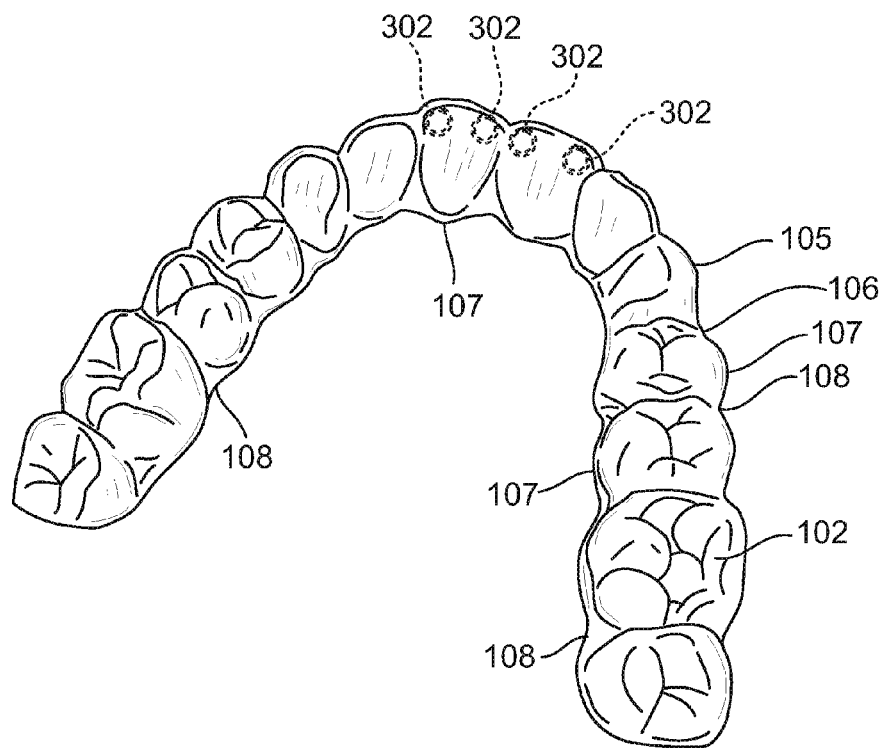
FIG. 6 is a bottom perspective view of an upper component of the oral appliance of FIG. 1.

Upper component 102 includes a plurality of raised surfaces 302 (depicted in FIGS. 3 and 6). In the depicted embodiment, there are four raised surfaces 302 located at the lingual incisal edges of the central incisors. In certain embodiments, raised surfaces 302 can be hemispherical in shape and can have an approximate diameter of 2 millimeters and a height of 2 millimeters. Certain embodiments can include 2-8 raised surfaces located at the lingual incisal edges of the lateral and/or central incisors. It has been found that inclusion of raised surfaces 302 on upper component 102 can stimulate the tongue to reposition itself toward raised surfaces 302 while a user is awake and/or sleeping. It has also been found that positioning the tongue toward the roof of the mouth and forward (away from the throat and toward a user's lips) is preferred to avoid constriction of the user's airway during sleep.

Lower component 104 is configured to be received on a user's lower (mandibular) teeth and is formed to substantially conform to the contours of certain of the user's lower teeth. Lower component 104 includes a lower segment 110 that spans the interior of the entire lower dental arch, including behind the rearmost molars. In certain embodiments, lower segment 110 may not span the user's entire lower dental arch. In the depicted embodiment, lower segment 110 extends behind the anterior teeth (incisors and cuspids) and does not extend over the top or immediately in front of the anterior teeth. It has been found that such a configuration can facilitate talking and/or drinking while wearing oral appliance 100. Lower segment 110 also extends behind the posterior teeth (bicuspids and molars) and extends over the top and immediately in front of the posterior teeth. In certain embodiments, lower segment 110 may extend over the top and immediately in front of the cuspids as well as the posterior teeth.

As depicted in FIG. 3, for example, the inter-arch portion of lower segment 110 includes interior flanges 306 that can extend as deep into a user's mouth as possible without impinging on the soft tissue and without discomfort. In the event that lingual tori are present, interior flanges 306 can accommodate for them without affecting the extent to which the interior flanges 306 extend rearward (toward the throat and away from a user's lips). Interior flanges 306 can have a thickness of greater than about 3 millimeters, but not so thick as to cause discomfort to the tongue when it rests in the bottom of the mouth. It has been found that such thickness can provide improved durability of oral appliance 100. It has also been found that such thickness can leave less room for the tongue at the bottom of the mouth, thereby encouraging the tongue to assume its natural position in the roof of the mouth. The tongue should be able to rest comfortably in the bottom of the mouth as well, as such positioning may be used if a user of the oral appliance is mouth breathing, for example, due to congestion of the nasal cavity.

As also depicted in FIG. 3, for example, lower segment 110 also includes ridges 304 disposed on opposing sides of lower segment 110. Ridges 304 comprise hemicylindrical ropes and can be about 3-5 millimeters in diameter and can extend about 1-1.5 centimeters anteriorly and upward from the distolingual corners of lower segment 110. It has been found that ridges 304 can prompt the tongue to assume its natural position upward of ridges 304 in the roof of the mouth. As mentioned above, it has been found that tongue advancement toward the roof of the mouth and forward (away from the throat and toward a user's lips) can be preferred to avoid constriction of the user's airway during sleep.

Lower component 104 also includes upper segments 112 disposed on either side of lower segment 110. Upper segments 112 are configured to matingly engage a portion of upper component 102 such that upper component 102 can be maintained in a desired posterior/anterior position relative to lower component 104. Upper component 102 can be disengaged from lower component 104 by opening a user's mouth, thereby increasing the vertical distance between a user's teeth. Whether the user's mouth is open or closed, however, the configuration of the lower and upper components 104 and 102 allows for non-restricted space between the teeth at the anterior of the mouth. It has been found that this anterior space can facilitate talking and/or drinking while wearing oral appliance 100. In the depicted embodiment, upper segments 112 are formed to substantially conform to the exterior and about half of the lower contour of the portion of upper component 102 that is formed for a user's molars and second bicuspids. Upper segments 112 include maxillary labial flanges 113 that extend upward to about the height of the tops of the crowns of a user's teeth. Maxillary labial flanges 113 include a flat upper edge 115 and curved ends toward the rear of upper segments 112.

Each upper segment 112 includes a first portion 116 (depicted in FIG. 4, for example) secured to lower segment 110 and a second portion that is not secured to lower segment 110. It is preferred that the thickness of upper segment 112 not exceed 1 centimeter. There is a slit 117 between first portion 116 and the second portion. The second portion of upper segment 112 is operably connected to the first portion 116 of upper segment 112 by a threaded element 114, such as a jack screw, for example. Slit 117 and threaded element 114 are disposed parallel to each other. This is in contrast to the prior art appliance of FIG. 7, wherein slit 117 and threaded element 702 are not parallel to each other. Manipulating threaded element 114 in a first rotational direction causes the corresponding second portion of upper segment 112 to be displaced toward the operably connected first portion 116 and thus anteriorly (away from the throat and toward a user's lips) relative to lower segment 110. Conversely, manipulating threaded element 114 in a second rotational direction that is opposite the first rotational direction causes the corresponding second portion of upper segment 112 to be displaced away from the operably connected first portion 116 and thus posteriorly (away from the lips and toward a user's throat) relative to lower segment 110. Manipulation of threaded elements 114 can allow adjustment of oral appliance 100 to provide a desired mandibular anterior/posterior positioning for a user.

Figure 4:
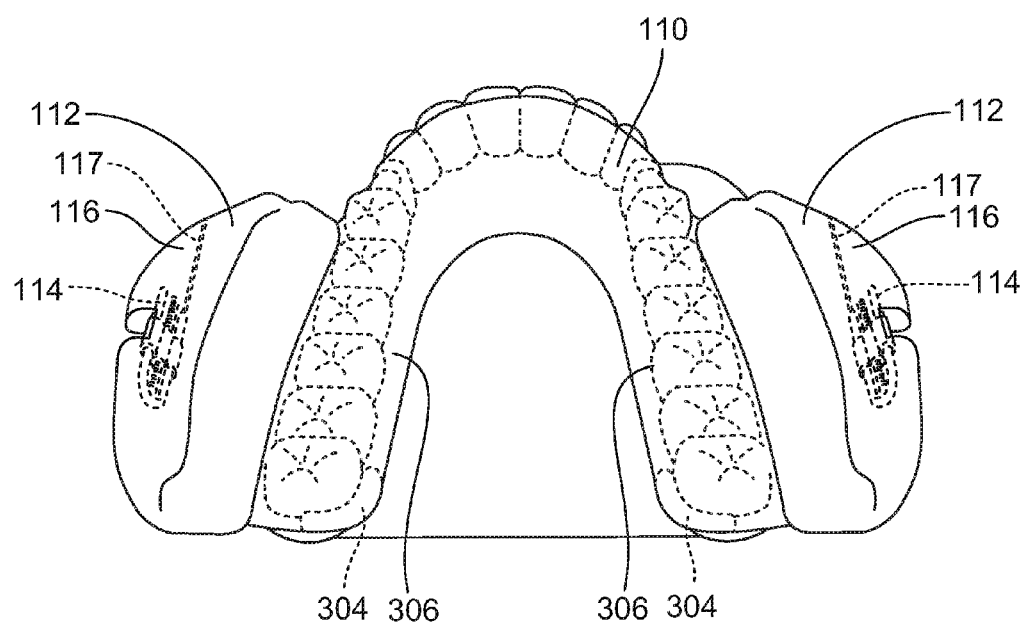
FIG. 4 is a top view of a lower component of the oral appliance of FIG. 1.
Figure 5:
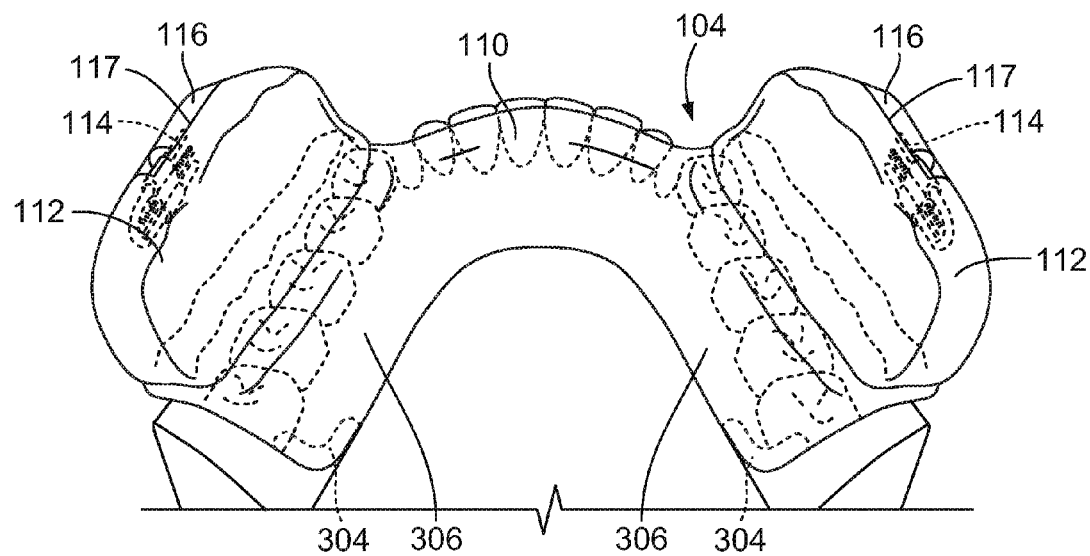
FIG. 5 is a top perspective view of a lower component of the oral appliance of FIG. 1.
Figure 7:
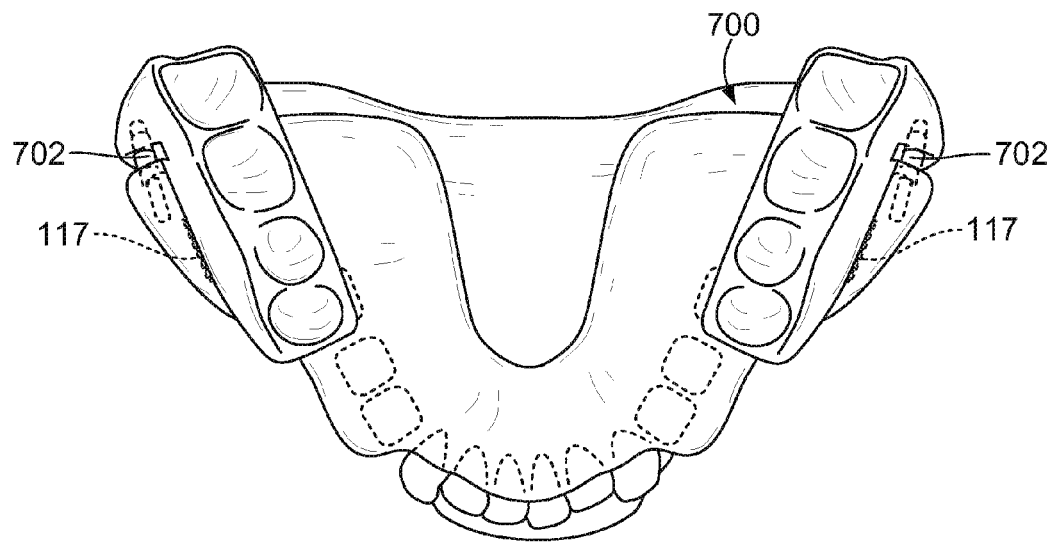
FIG. 7 is a top view of a lower component of a prior art oral appliance.
Figure 21:
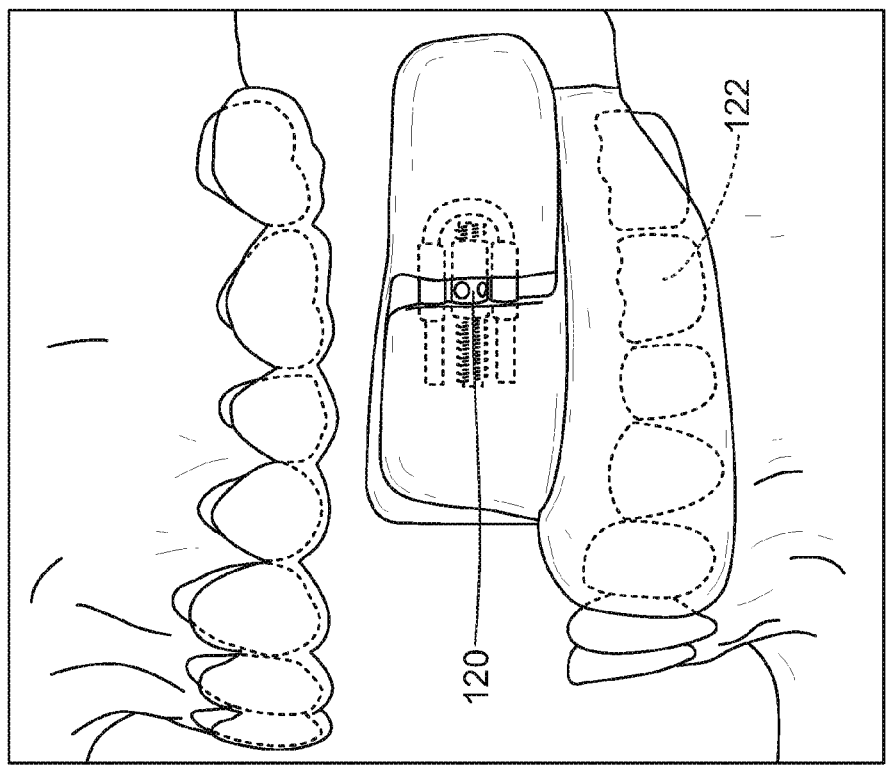
FIG. 21 is a side view of the oral appliance of FIG. 1.

As depicted, for example, in FIG. 4, each threaded element 114 is disposed within first portion 116 of upper segment 112 and within second portion of upper segment 112 such that threaded elements 114 are disposed substantially parallel to each other. First and second portions should not extend so far as to stretch a user's cheeks, which could inhibit closure of the lips and/or cause discomfort. It has been found that disposing threaded elements 114 substantially parallel to each other can provide for improved durability relative to known configurations. For example, FIG. 7 depicts a prior art oral appliance 700 including threaded elements 702 that are aligned with a user's dental arch, and are not disposed substantially parallel to each other. It has been found that such devices can be prone to breakage during manipulation of threaded elements 702 due to excessive lateral forces being exerted on portions of the device. Referring to FIG. 21, it has also been found to be advantageous to position the threaded element 114 so that the center 120 of threaded element 114 lines up as closely as possible with the center of maxillary first molar 122.

In certain embodiments, an oral appliance as described above can be configured so that the lower component is unitary, such that the upper segment and lower segment are not movable relative to each other. Such embodiments would not include threaded elements, but could otherwise be the same as the embodiment depicted in FIGS. 1-6.

Methods of making and using oral appliances as described herein are also part of the present invention. In an embodiment, a method of making such an oral appliance can include: (1) making casts of a user's dental arches; (2) determining and recording a patient's bite position using a bite registration device, such as a bite registration device of the type described below; (3) mounting the casts and bite registration device on a dental articulator; (4) forming the upper component from a suitable material; and (5) forming the lower component from a suitable material. In embodiments where the oral appliance includes an adjustable lower component, the method of making can further include: (6) cutting the lower component about a horizontal plane that is substantially parallel to the tops of a user's lower posterior teeth and the bottoms of the user's upper posterior teeth, the horizontal cut preferably positioned as discussed more fully below, thereby providing from the lower component a lower segment and two upper segments; (7) making a vertical cut in each upper segment to accommodate a threaded element; and (8) operably connecting a portion of each upper segment to a portion of material that is secured to the corresponding portion of the lower segment using a threaded element, such that the threaded elements are substantially parallel to each other when the upper segments are attached to the lower segment, and such that each upper segment can be displaced posteriorly/anteriorly relative to the lower segment using the threaded elements.

Figure 17:
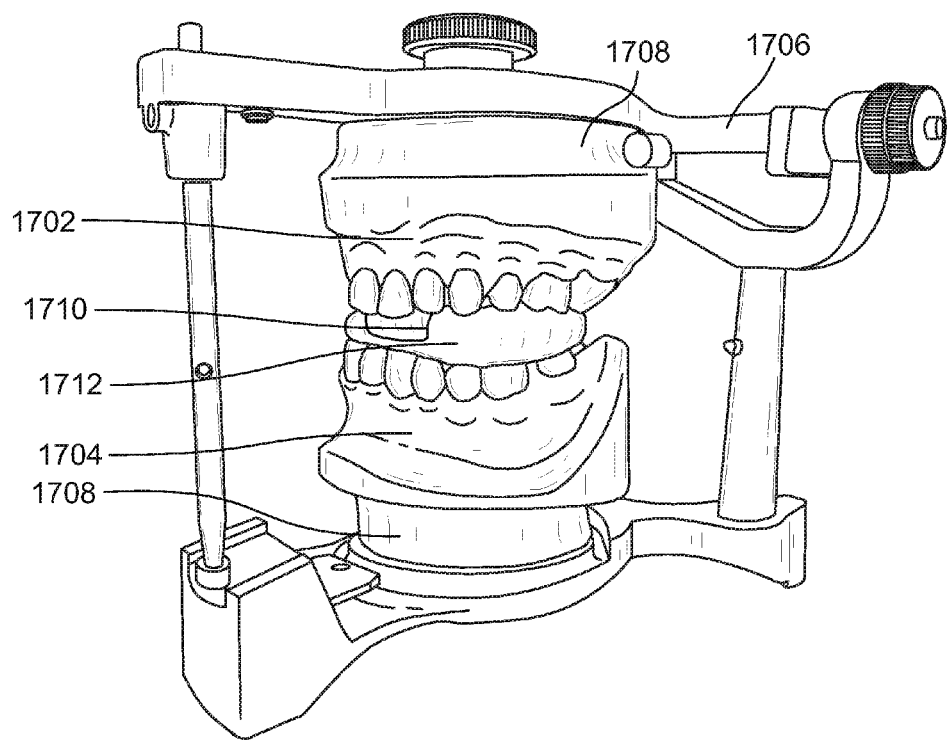
FIG. 17 depicts a step of a bite registration process used in accordance with an embodiment of the present technology.

In an embodiment, a method of making an oral appliance as described herein can include the following steps. A dental model using a type-4 dental plaster conforming to ISO standard 6873:1998, such as Hydrocal 105, for example, is poured into an upper impression and a lower impression. Once the impressions set, they become casts. The lower cast is surveyed and undercuts are removed, in both hard and soft tissue. Undercuts are waxed and trimmed on the casts to permit easy insertion and removal of the appliance from the mouth. Casts are mounted on a plasterless dental articulator with a vertical stop according to the prescribed bite as provided by a bite registration device, such as the bite registration device described below, for example. FIG. 17 depicts an upper cast 1702 and a lower cast 1704 mounted on an articulator 1706 using plaster 1708 to hold the casts in place on the articulator 1706. Bite registration devices 1710 and bite recording material 1712 are depicted and are used to record the prescribed bite.

Figure 18:
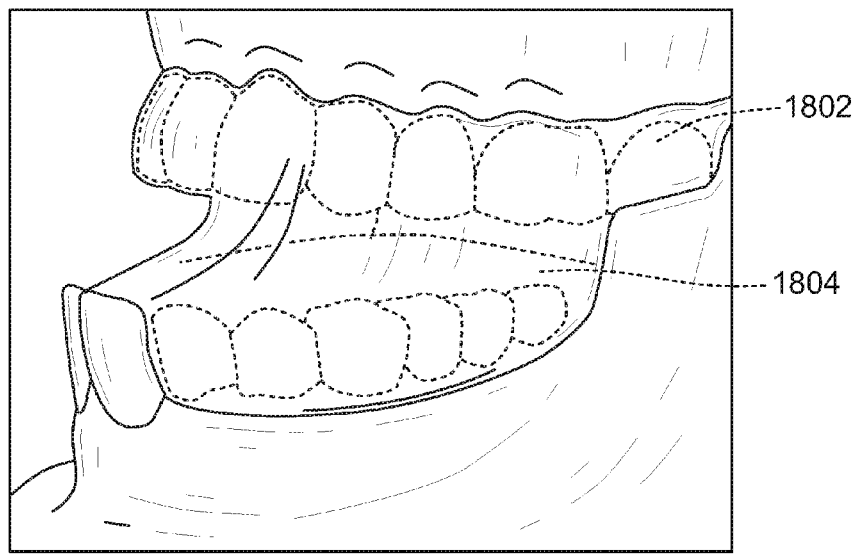
FIG. 18 depicts a step of an oral appliance forming process used in accordance with an embodiment of the present technology.

A vacuum formed dental splint (the upper component), formed of a polypropylene copolymer that is non-retentive to methyl-methacrylate, is made over the ummounted upper cast. The upper component is removed from the unmounted upper cast and trimmed slightly so it fits over the articulator-mounted upper cast. With the vacuum-formed upper component in place on the upper cast, the initial stage of the lower component is made of blue tinted or white tooth-colored (or other colored) methyl-methacrylate and processed in a pressure pot. FIG. 18 depicts upper component 1802 and lower component 1804.

Figure 19:
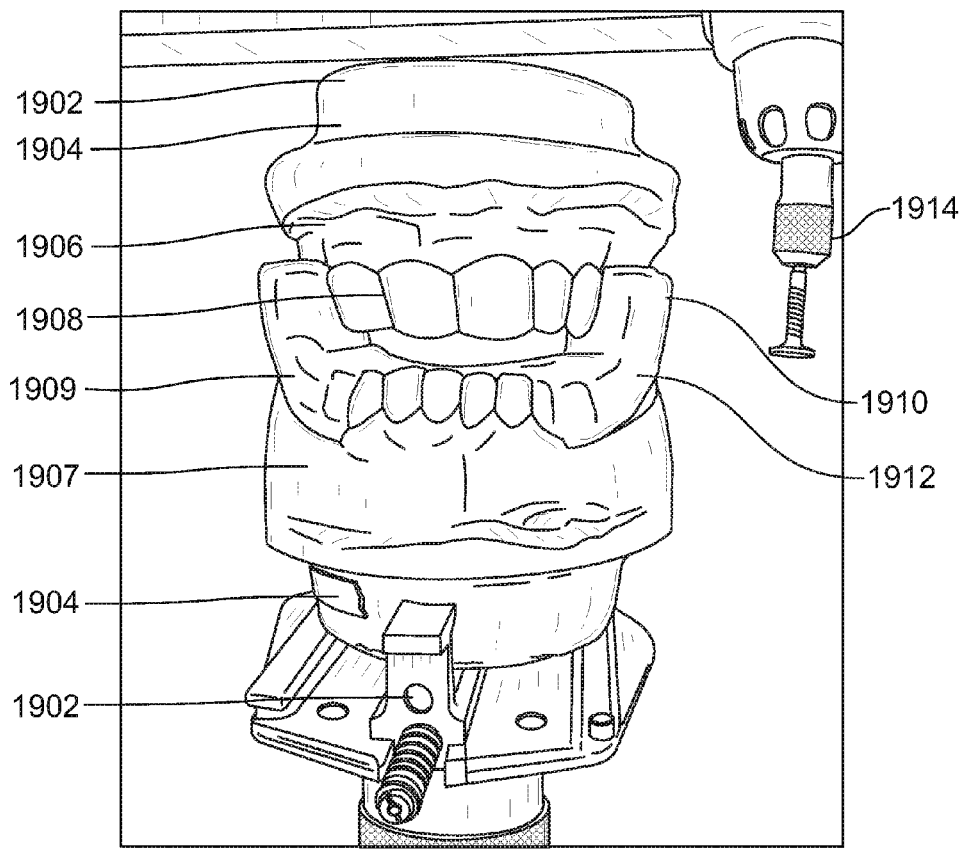
FIG. 19 depicts a step of an oral appliance forming process used in accordance with an embodiment of the present technology.

The case, which includes the articulator, the plaster, the casts and the formed upper and lower components all assembled, is removed from the pressure pot and the casts are removed from the articulator, but the casts are not separated from the upper and lower components. The initially-processed case is mounted on a fully adjustable cast holder, secured in place by the lower cast. FIG. 19 depicts such a cast holder and depicts: articulator 1902, plaster 1904, upper cast 1906, lower cast 1907, upper component 1908, and lower component 1909.

Figure 20:
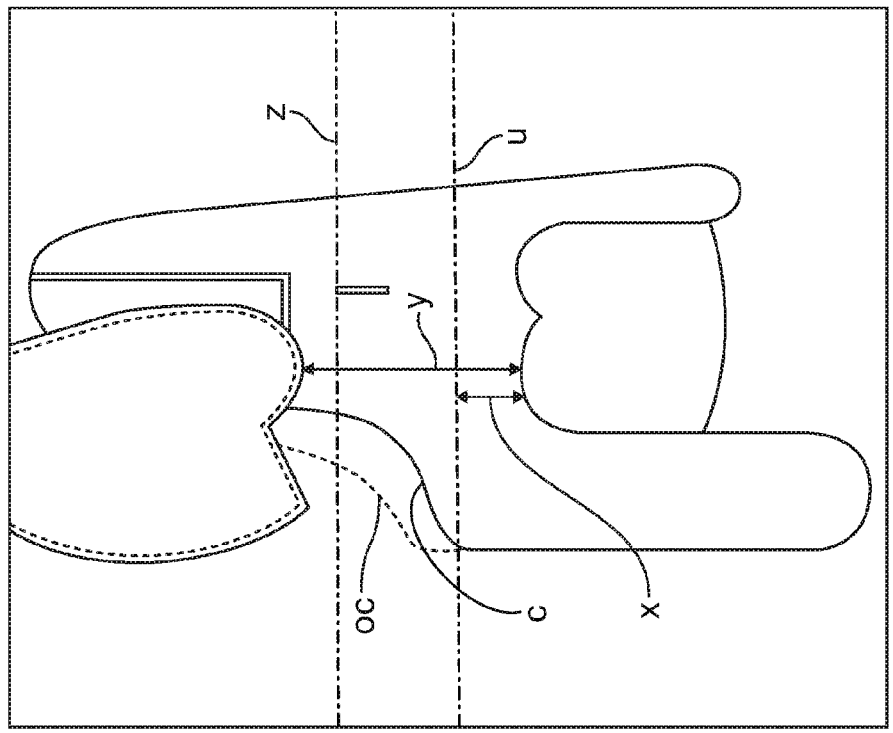
FIG. 20 is a front cut view of the oral appliance of FIG. 1.

The case mounted on a cast holder is surveyed on a dental surveyor to determine the optimal positioning for the horizontal plane on which the case will slide when adjusted horizontally. The optimal plane divides the distance between the upper teeth and the lower teeth, and is parallel to the maxillary plane of occlusion. As depicted in FIG. 19, a saw 1914 can be used to make a horizontal cut, thereby separating lower component 1909 into an upper segment 1910 and a lower segment 1912. Turning now to FIG. 20, the location of the horizontal cut in certain embodiments is described. In that regard, the horizontal cut h is made so that the distance x below the cut is less than or equal to approximately ⅓ of the distance y between the corresponding upper and lower teeth (as shown in FIG. 20).

In the prior art devices, the horizontal cut was made at approximately z (as also shown in FIG. 20). Making the cut at u, however, allows for a more sloped, hollowed contour c, which transverses the front portion of upper segment 1910, as compared with contour oc that could be made with prior art devices. Contour c allows for increased tongue space, particularly for the anterior sides of the tongue.

The case is then surveyed to determine the locations for the vertical cuts in the upper segment 1910 that determine the path of anterior adjustable movement of the appliance. The vertical cuts are positioned so that the anterior member, which is the fixed part holding the adjustment screw, has good mechanical support and will not fracture with lateral bruxism pressures. The bulk of the strength of the labial flange for resisting lateral bruxism pressures is in this part of the maxillary labial flange. The vertical cuts are made so that the adjustment screws are set substantially parallel to each other and the path for adjustment is directed anteriorly and parallel to the path of expansion of the screw. The vertical cuts are perpendicular to the horizontal path of movement determined in the previous step.

The upper cast with the upper component attached are removed from the lower component. The horizontal cuts are made first, using a circular disc saw with a thickness of about 0.12-0.15 millimeters, as depicted, for example, in FIG. 19. The saw is rigidly mounted and the dental appliance is passed through on the cast holder. The maxillary flanges are thus cut off the appliance. The vertical cuts are then made in the detached maxillary flanges using the same disc saw blade. The lower horizontal cut surface is polished. The inner vertical cut component is again cut vertically along the occlusal groove separating the buccal and lingual cusps and the inner surface polished. The lingual position of the upper segment is contoured to create space for the lateral borders of the tongue. The resulting contour c is shown in FIG. 20.

Separating medium is placed on the appropriate surfaces and the upper cut segment luted to the upper model with the splint still in place on the articulator. The upper model is then luted to the lower model with the casts stabilized to each other in their original position. The adjustment screw separator/protector is then trimmed to fit and luted to the maxillary cut and adapted flange. Wet methyl-methacrylate is then applied so that the anterior part of the adjustment screw is bonded to the lower part of the device and the posterior part of the adjustment screw is bonded to the labial part of the cut edge of the maxillary flange.

The uncured methyl-methacrylate is then processed in the pressure pot. The entire lower component is trimmed and polished. The upper component splint in propylene copolymer is trimmed with a fine scissors so it fits over the teeth but does not contact gingiva. The factory-inserted separating seal material in the adjustment screw is removed. Turning the adjustment screw now moves the mandible anteriorly while the maxilla does not move. Should the distal bulk of the maxillary flange impinge on the cheek muscles and cause discomfort distal to or in the second molar area of the cheek, the maxillary flange of the lower component may be cut off distal to the maxillary first molar.

As mentioned above, the present technology also includes a bite registration device for use by dentists to determine and record a patient bite position for a laboratory to fabricate an oral dental device.

Embodiments of the present technology can allow a dentist to determine a patient's mandibular jaw position in space with the patient's lips together and record a full arch bite. Having the lips together with the bite registration in the mouth can closely simulate the patient with a future oral dental device in his or her mouth.

Embodiments of the present technology can be used by dentists to determine and record their prescribed therapeutic mandibular jaw position when fabricating an oral dental device to treat, for example, temporomandibular joint dysfunction, snoring, sleep apnea, and/or other dental situations that are appropriately treated with oral appliances.

In certain embodiments, the bite registration device extends posteriorly to the area of cuspids or bicuspids, depending on the size of the patient's mouth. Each device can have one or more convex male protrusion(s) on one side and one or more concave female receptacles on the opposite side. The male protrusion(s) and the concave female receptacle(s) correspond to each other in location, so the devices are stackable and snap into one another, becoming one unit. For the upper arch, the side with the convex male protrusion(s) faces up, and the protrusion(s) is/are located behind the maxillary anterior teeth, with the opposite side being planar and having the female receptacle(s). For the lower arch, the side with the convex male protrusion(s) faces down, and the protrusion(s) is/are behind the mandibular anterior teeth, with the opposite side being planar and having the female receptacle(s). Such a configuration for opposing bite registration devices allows the planar surfaces of the devices (with female receptacle(s)) to slide against each other into the correct position prescribed by the dentist. In a preferred embodiment, the number of bite registration devices used on a particular patient can be a maximum number that the patient can comfortably hold in his or her mouth while his or her lips are completely closed.

A dentist can stack and snap as many bite registration devices together to establish a desired vertical dimension corresponding to the thickness of the stacked bite registration devices. Once the bite registration devices are in place, the dentist can manually move the mandible from right to left and front to back until the patient's mandible is in the position that the dentist desires. The dentist can then squirt or position bite-recording material between the posterior teeth and in front of the anterior teeth to make the impressions of the teeth. The bite-recording material mechanically attaches to the bite registration device and the desired full arch bite registration is complete.

Figure 8:
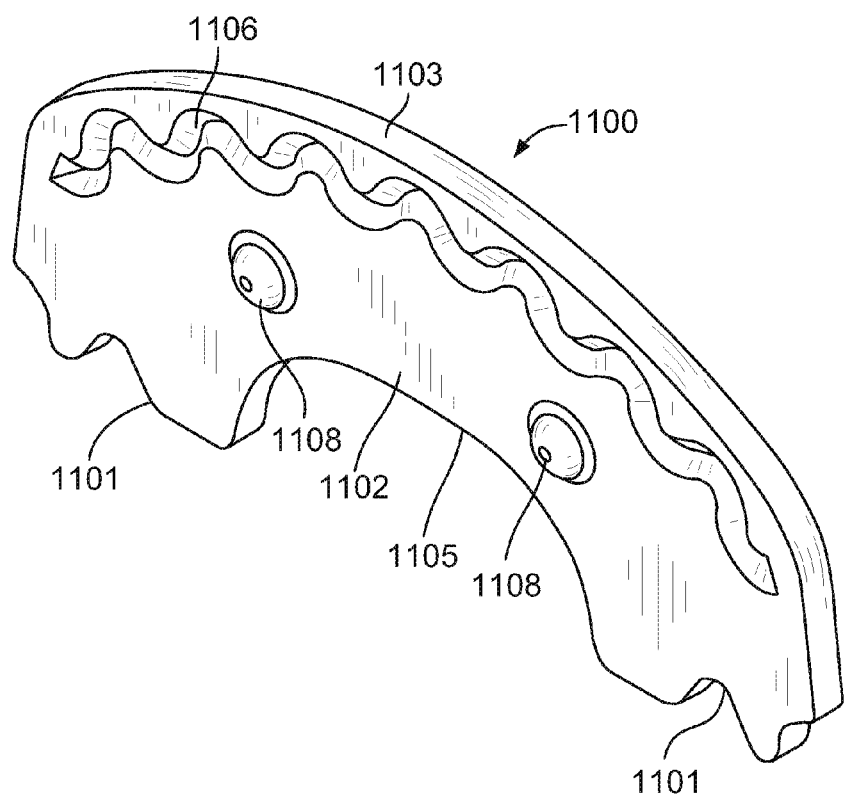
FIG. 8 is a top perspective view of a bite registration device used in accordance with an embodiment of the present technology.
Figure 9:
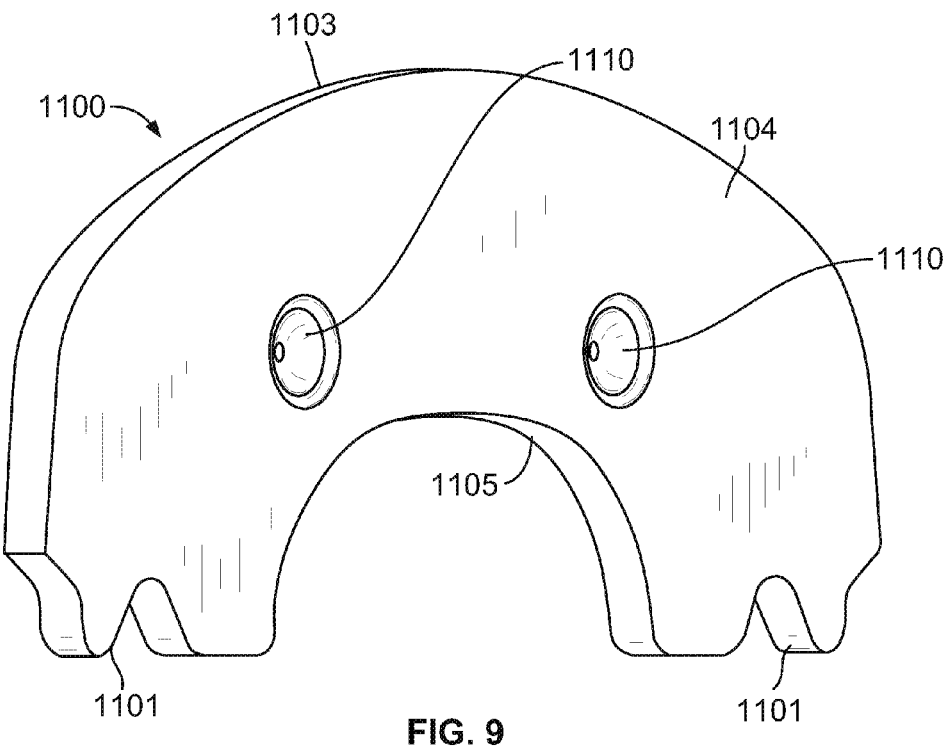
FIG. 9 is a bottom perspective view of the bite registration device of FIG. 8.
Figure 10:
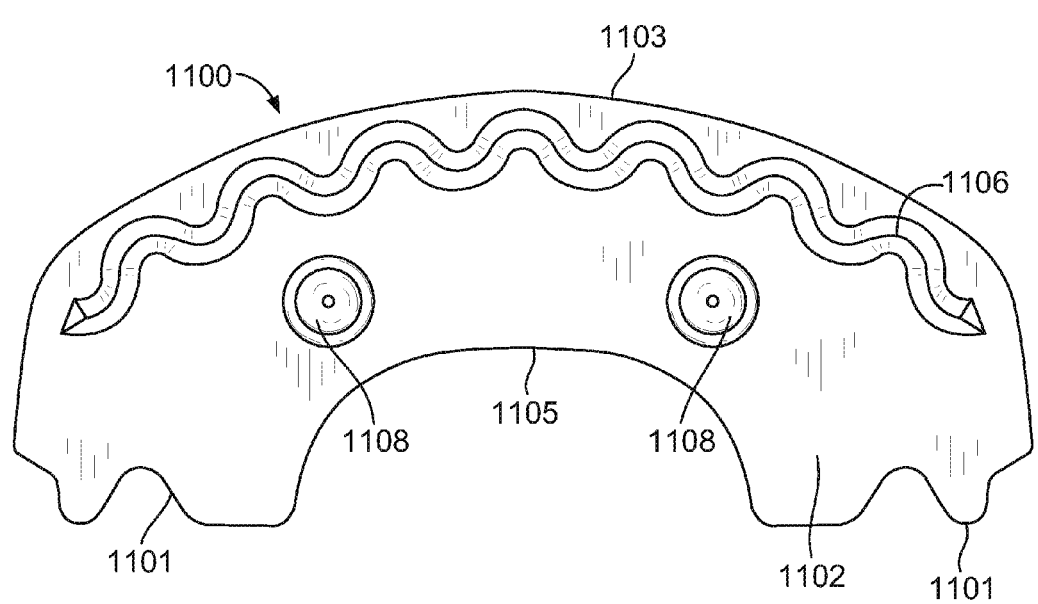
FIG. 10 is a top view of the bite registration device of FIG. 8.
Figure 11:
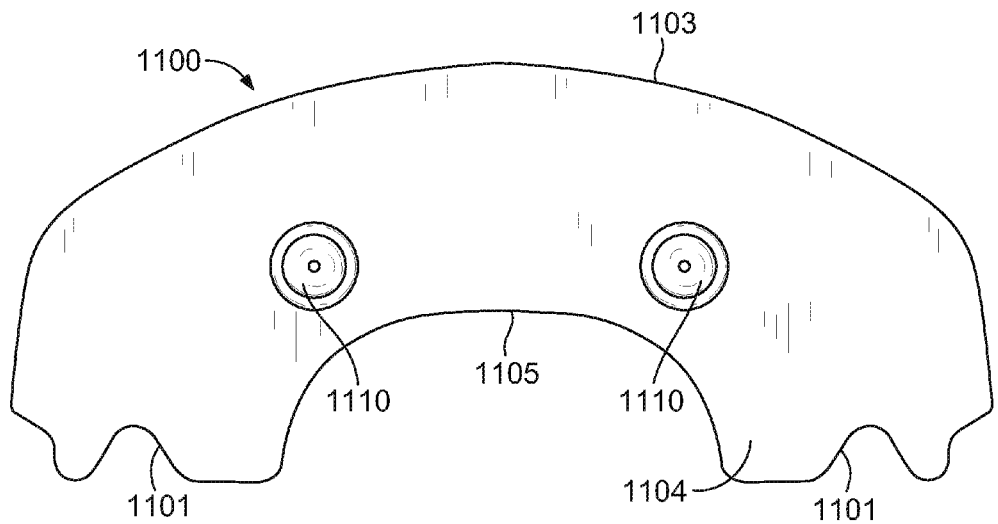
FIG. 11 is a bottom view of the bite registration device of FIG. 8.
Figure 15:
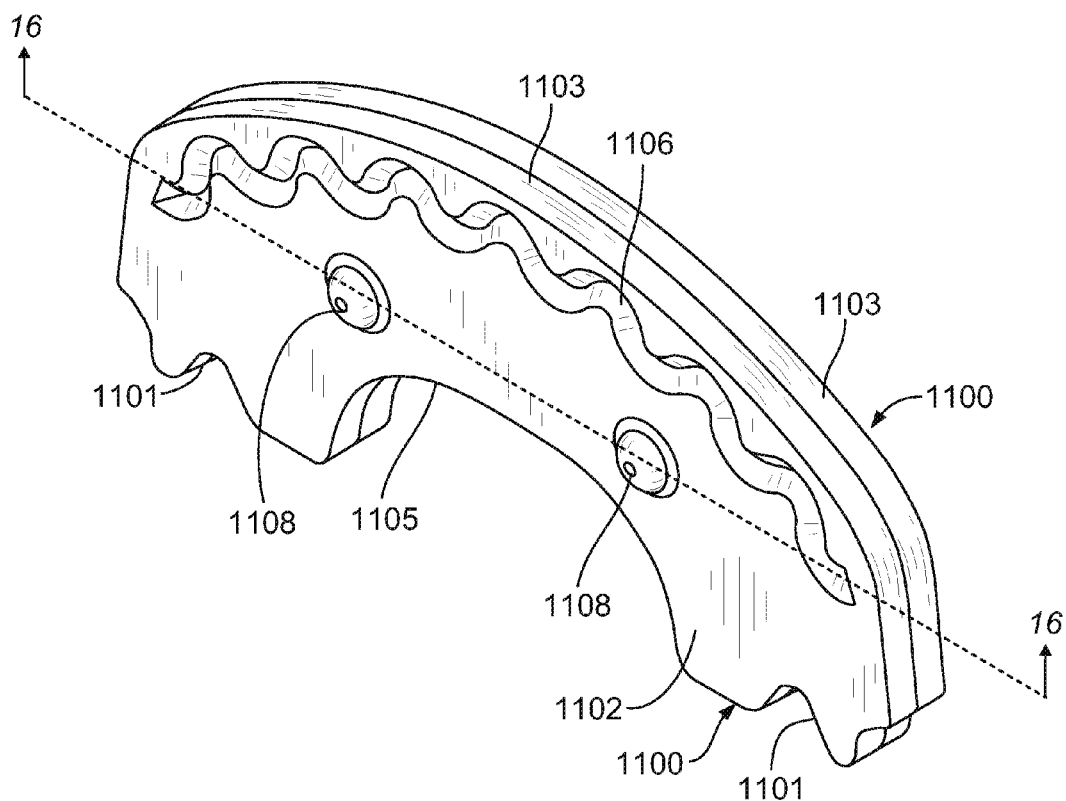
FIG. 15 is a top perspective view of the bite registration device of FIG. 8 stacked on top of a second bite registration device.
Figure 16:
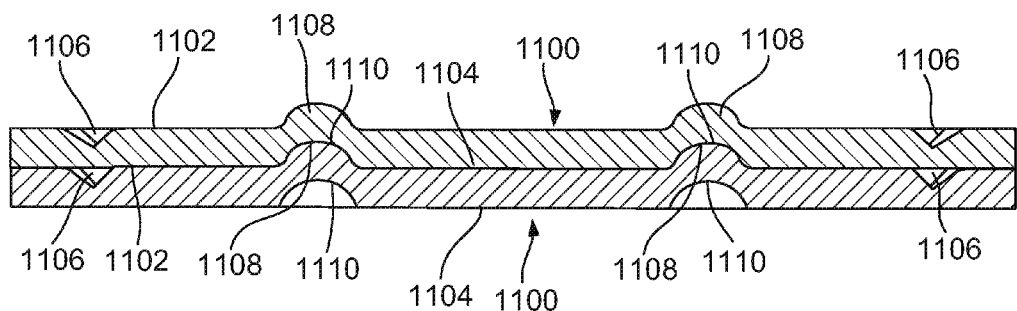
FIG. 16 is a sectional view of the bite registration devices of FIG. 15 about the line 16-16.

FIG. 8 is a top perspective view of a bite registration device 1100 used in accordance with an embodiment of the present technology. FIGS. 9-14 provide various other views of bite registration device 1100. FIGS. 15-16 depict two bite registration devices 1100 stacked together.

Bite registration device 1100 includes an arched front edge 1103 configured to accommodate the oral cavity such that a patient's lips can be completely closed adjacent to arched front edge 1103 while bite registration device 1100 is maintained within the patient's mouth. Bite registration device 1100 includes arched rear edge 1105 opposite arched front edge 1103. Arched rear edge 105 is configured to accommodate a patient's tongue while bite registration device 1100 is maintained within the patient's mouth. Bite registration device 1100 includes non-uniform ends 1101 opposite arched front edge 1103. Non-uniform ends 1101 comprise non-linear edges that connect arched front edge 1103 to arched rear edge 1105. Non-uniform ends 1101 are configured to aid in retention of a bite-recording material during the bite registration process. In certain embodiments, bite registration devices may be provided in a different shape. In certain embodiments, bite registration device 1100 can be made of HDPE (high density polyethylene), LDPE (low density polyethylene), or PP (polypropylene), for example.

Figure 12:
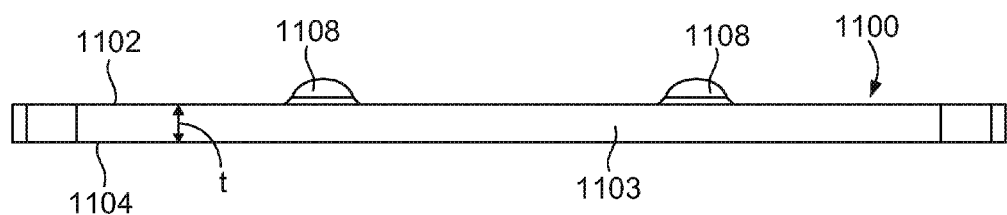
FIG. 12 is a front side view of the bite registration device of FIG. 8.
Figure 13:
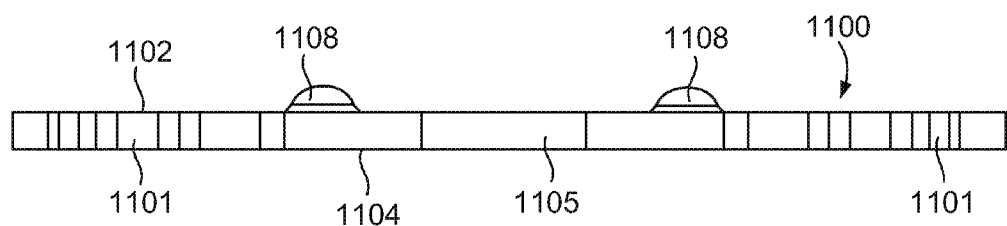
FIG. 13 is a rear side view of the bite registration device of FIG. 8.
Figure 14:
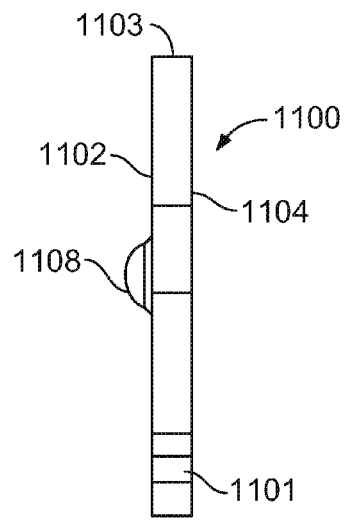
FIG. 14 is an end side view of the bite registration device of FIG. 8.

In the depicted embodiment, bite registration device 1100 is generally planar and includes a top surface 1102, a bottom surface 1104 (depicted in FIG. 9), and a thickness t (depicted in FIG. 12). In certain embodiments, thickness t can be about 1.5 millimeters, for example. Bottom surface 1104 is configured to be disposed away from a patient's teeth during the bite registration process. Top surface 1102 is configured to be disposed toward the patient's teeth during the bite registration process. Bottom surface 1104 does not include any protrusions, such that two opposing bite registration devices can be slidably adjusted when the bottom surfaces are in contact and the top surfaces face opposite directions (toward the patient's teeth). This configuration can allow opposing bite registration devices to be slidably adjusted to provide a desired position for a patient's mandibular (lower) arch relative to the patient's maxillary (upper) arch during the bite registration process.

In the depicted embodiment, top surface 1102 includes a groove 1106 configured to aid in retention of a bite-recording material during the bite registration process. In the depicted embodiment, groove 1106 is generally wave-shaped and disposed adjacent to arched edge 1103. In other embodiments, other textures and/or multiple grooves disposed in top surface 1102 can be used to aid in retention of a bite-recording material during the bite registration process.

In the depicted embodiment, top surface 1102 includes protrusions 1108 that extend upwardly from top surface 1102. Protrusions 1108 are configured to matingly engage receptacles 1110 (depicted in FIG. 9) disposed on bottom surface 1104 of bite registration device 1100, such that a first bite registration device 1100 can be maintained in stacked relation with a second bite registration device 1100, as depicted in FIGS. 15-16. Stacking two such bite registration devices provides a bite registration device with double the thickness. Any number of such bite registration devices can be stacked to provide a desired thickness. The thickness of such a bite registration device can thus be customized in order to allow a dentist to select a custom distance between a patient's maxillary (upper) and mandibular (lower) arches.

In the depicted embodiment, protrusions 1108 and receptacles 1110 are configured to provide a tension fit between stacked bite registration devices 1100. In the embodiment shown, there are two protrusions 1108 and two receptacles 1110 that are circular in shape. Other embodiments may include one protrusion and one receptacle or three or more protrusions and an equal number of receptacles. Other embodiments may include differently shaped protrusions and receptacles, such as rectangular, triangular, oval, and/or square shaped, for example. In the embodiment shown, bite registration devices 1100 are maintained in stacked relation by matingly engaging protrusions 1108 and receptacles 1110. In other embodiments, however, bite registration devices can be maintained in stacked relation using other attachment methods.

In operation, any number of bite registration devices, as described herein, can be stacked to provide a desired thickness, thereby allowing a dentist to select a custom distance between a patient's maxillary (upper) and mandibular (lower) arches. Also, the arched front edge of bite registration devices described herein is configured such that none of the bite registration device extends beyond a patient's lips when the bite registration device is maintained in the patient's mouth, thereby allowing the patient to completely close his or her lips during the bite registration process. Also, certain bite registration devices described herein can aid in retention of a bite-recording material during the bite registration process.

The present invention also includes methods of making and using bite registration devices as described herein. For example, in an embodiment, a method of using a bite registration device can include: stacking two or more bite registration devices such that they are maintained in stacked relation, thereby providing a first bite registration device; positioning the first bite registration device into a patient's mouth; positioning a second bite registration device into the patient's mouth such that the first bite registration device and the second bite registration device abut at a planar surface; slidably adjusting the relative position of the first bite registration device and the second bite registration device while maintaining abutment therebetween by manipulating the position of the patient's mandible; applying a bite-recording material to the first and second bite registration devices around the patient's teeth and gums; and allowing the bite-recording material to mechanically adhere to the first and second bite registration devices, thereby capturing the patient's bite position. The bite registration device can then be removed and used during fabrication of an oral appliance. For example, stone casts can be mounted on an articulator with the bite registration between the maxillary and mandibular arches in the exact position that the dentist prescribes.

Thus, as described herein, embodiments of the present invention provide several modifications to the prior art appliance of FIG. 7, including, but not limited to, the following: (A) the threaded elements 114 and slits 117 are disposed parallel to each other; (B) threaded elements 114 are substantially parallel to each other; (C) the thickness of the upper segment is less than or equal to 1 centimeter; (D) the location of the screw separator is as close to the middle of the maxillary first molar as possible; (E) the lingual contour above the lower segment provides for increased room for the lateral border of the tongue; (F) the raised surfaces 302 of the upper component provide stimulation of the tongue reflex to move the tongue toward the roof of the mouth; (G) the increased bulk on the lower linguals helps lift the tongue position to the roof of the mouth; (H) the upper component 102 and/or the lower component 104 can comprise a non-clear material, such as a translucent blue or opaque tooth color; and (I) the protrusions of the bite registration device provide for convenient stacking and use within a patient's mouth.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. A bite registration device configured for use in making an oral appliance comprising:
    a first surface including a protrusion;
    a second surface opposite the first surface, the second surface including a receptacle,
    arched edges comprising (i) an arched front edge connecting the first surface and the second surface and (ii) an arched rear edge connecting the first surface and the second surface and defining a vertically uninterrupted gap, wherein the front edge and rear edge are connected by ends that are located on opposite sides of the gap,
    a wave-shaped groove on the first surface that is configured to retain bite-recording material, and
    wherein the bite registration device is configured to be maintained in stacked relation and connected to a second bite registration device by snapably mating the protrusion of the bite registration device with a receptacle of the second bite registration device.

2. The bite registration device of claim 1, wherein the groove is positioned closer to the arched front edge than the arched rear edge.

3. The bite registration device of claim 1, wherein the arched front edge is configured to be adjacent to a user's lips when the bite registration device is maintained in the user's mouth such that the bite registration device does not protrude beyond the user's closed lips when the bite registration device is maintained in the user's mouth.

4. The bite registration device of claim 3, wherein the arched rear edge is configured to be adjacent to the user's tongue when the bite registration device is maintained in the user's mouth and the user's tongue can pass through the gap.

5. The bite registration device of claim 4, wherein the ends are jagged edges that are configured to retain bite-recording material on the bite registration device.

6. The bite registration device of claim 1, wherein the first surface is configured to face toward a user's teeth during a bite registration procedure.

7. The bite registration device of claim 1, wherein the second surface is configured to face away from a user's teeth during a bite registration procedure.

8. The bite registration device of claim 1, wherein the second surface is planar.

9. The bite registration device of claim 1,
    wherein the protrusion has a rounded convex top surface and the receptacle has a rounded concave shape.

10. A bite registration device configured for use in making an oral appliance comprising:
    a first surface including a protrusion;
    a second surface opposite the first surface, the second surface including a receptacle,
    arched edges comprising (i) an arched front edge connecting the first surface and the second surface and (ii) an arched rear edge connecting the first surface and the second surface and defining a vertically uninterrupted gap, wherein the front edge and rear edge are connected by jagged ends that are located on opposite sides of the gap, the jagged ends being configured to retain bite-recording material,
    a wave-shaped groove on the first surface that is configured to retain bite-recording material, wherein the groove is positioned closer to the arched front edge than the arched rear edge, and
    wherein the height that the protrusion extends above the first surface is less than the thickness of the bite registration device between the first surface and the second surface, and
    wherein the bite registration device is configured to be maintained in stacked relation to a second bite registration device by mating the protrusion of the bite registration device with a receptacle of the second bite registration device.

11. The bite registration device of claim 10, wherein the bite registration device is connected to a second bite registration device by snapably mating the protrusion of the bite registration device with a receptacle of the second bite registration device.

12. The bite registration device of claim 10, wherein the protrusion has a rounded convex top surface and the receptacle has a concave shape.

* * * * *